United States Patent
O'Donnell et al.

(10) Patent No.: US 7,666,356 B2
(45) Date of Patent: Feb. 23, 2010

(54) TRACE SAMPLING

(75) Inventors: Daniel O'Donnell, Orlando, FL (US); Edward E. A. Bromberg, Orlando, FL (US); Paul Crabb, Orlando, FL (US); Ravi Konduri, Waltham, MA (US); C. Andrew Helm, Oviedo, FL (US); David H. Fine, Orlando, FL (US)

(73) Assignee: L-3 Communications Cyterra Corporation, Orlando, FL (US)

( * ) Notice: Subject to any disclaimer, the term of this patent is extended or adjusted under 35 U.S.C. 154(b) by 779 days.

(21) Appl. No.: 11/425,313

(22) Filed: Jun. 20, 2006

(65) Prior Publication Data
US 2007/0086925 A1    Apr. 19, 2007

Related U.S. Application Data

(60) Provisional application No. 60/691,778, filed on Jun. 20, 2005, provisional application No. 60/700,039, filed on Jul. 18, 2005, provisional application No. 60/702,616, filed on Jul. 27, 2005, provisional application No. 60/743,083, filed on Dec. 29, 2005, provisional application No. 60/743,402, filed on Mar. 3, 2006.

(51) Int. Cl.
*G01N 1/24* (2006.01)
*G01N 21/00* (2006.01)

(52) U.S. Cl. ............... 422/82.05; 73/28.01; 73/863.23; 73/863.56

(58) Field of Classification Search .............. 422/82.05; 73/28.01, 863.23, 863.56
See application file for complete search history.

(56) References Cited

U.S. PATENT DOCUMENTS

| 4,045,997 | A | * | 9/1977 | Showalter et al. ............ 73/23.2 |
| 4,896,547 | A | | 1/1990 | Arney |
| 4,909,089 | A | | 3/1990 | Achter |
| 4,964,309 | A | | 10/1990 | Jenkins |
| 5,638,166 | A | | 6/1997 | Funsten et al. |
| 5,753,832 | A | | 5/1998 | Bromberg et al. |
| 5,760,314 | A | | 6/1998 | Bromberg |
| 5,915,268 | A | | 6/1999 | Linker |
| 6,073,499 | A | | 6/2000 | Settles |
| 6,334,365 | B1 | | 1/2002 | Linker |
| 6,375,697 | B2 | | 4/2002 | Davies |
| 6,406,918 | B1 | | 6/2002 | Bannister et al. |
| 6,708,572 | B2 | | 3/2004 | Jenkins |
| 6,790,249 | B2 | | 9/2004 | Davies |

(Continued)

OTHER PUBLICATIONS

International Search Report and Written Opinion issued in International Application No. PCT/US06/23908 mailed Apr. 7, 2008, 12 pages.

*Primary Examiner*—Jill Warden
*Assistant Examiner*—Paul S Hyun
(74) *Attorney, Agent, or Firm*—Fish & Richardson P.C.

(57) ABSTRACT

A trace sampling detection system includes a gathering device configured to gather particles through a handle-bar, a gate and an air-stream gatherer. A collection tube is configured to deposit gathered particles from the gathering device onto a portion of a sample media. A carousel wheel that includes the sample media is configured to rotate the sample wheel such that the portion of the sample media including the gathered particles is presented to an exothermic decomposition detector that detects, through an infrared sensor, the decomposition of the gathered particles.

20 Claims, 9 Drawing Sheets

U.S. PATENT DOCUMENTS

| | | |
|---|---|---|
| 6,840,122 B1 | 1/2005 | Jenkins |
| 7,141,786 B2 | 11/2006 | McGann |
| 7,180,441 B2 | 2/2007 | Rowe et al. |
| 2003/0234366 A1 | 12/2003 | Basch et al. |
| 2004/0014233 A1 | 1/2004 | Bannister et al. |
| 2004/0053421 A1 * | 3/2004 | Nguyen et al. ............ 436/172 |

* cited by examiner

600

```
┌─────────────────────────────────────┐
│ Gather particles through collection holes │
│                 610                 │
└─────────────────────────────────────┘
                   │
                   ▼
┌─────────────────────────────────────┐
│  Deposit gathered particles onto a  │
│             sample media            │
│                 620                 │
└─────────────────────────────────────┘
                   │
                   ▼
┌─────────────────────────────────────┐
│  Present the gathered particles to a │
│            detection unit           │
│                 630                 │
└─────────────────────────────────────┘
                   │
                   ▼
┌─────────────────────────────────────┐
│     Analyze the gathered particles   │
│                 640                 │
└─────────────────────────────────────┘
```

FIG. 6

TRACE SAMPLING

CROSS-REFERENCE

This application claims priority from U.S. Provisional Application Nos. 60/691,778, filed Jun. 20, 2005, and titled "Simplified Trace Sampling of People For Explosives"; 60/700,039, filed Jul. 18, 2005, and titled "Simplified Trace Sampling of People For Explosives"; 60/702,616, filed Jul. 27, 2005, and titled "Trace Explosives Detector Based Upon Detecting Exothermic Decomposition"; 60/743,083, filed Dec. 29, 2005, and titled "Energetic Material Detector For Explosive Trace Detection"; and 60/743,402, filed Mar. 3, 2006, and titled "Energetic Material Detector For Explosive Trace Detection." Each of these applications is incorporated by reference.

TECHNICAL FIELD

This disclosure relates to trace sampling to detect materials such as explosives.

BACKGROUND

In order to detect the presence of a material, such as explosives, particles of the material may be collected and analyzed.

SUMMARY

In one general aspect, a trace sampling detection system includes a gathering device configured to gather particles through each of several components. A handle-bar includes collection holes positioned to be adjacent to a user's hand when the user grips the handle-bar. The handle-bar is configured to dislodge and capture particles from the user's hand when the user grips and moves the handle-bar. A gate including a series of collection holes is positioned to be adjacent to the user's clothing when the user traverses the gate. The gate is configured to dislodge and capture particles from the user's clothing in response to pressure applied from the user. An air-stream gatherer including an outward vent and an in-drawing vent is positioned to enable objects, such as the user's feet, to be placed between the outward and in-drawing vents. The air-stream is configured to dislodge and capture particles from objects, such as the user's feet, that block the air-stream between the outward and in-drawing vent. A collection tube is configured to deposit gathered particles from the gathering device onto a portion of a sample media. A carousel wheel that includes the sample media is configured to rotate the sample wheel such that the portion of the sample media including the gathered particles is presented to an exothermic decomposition detector. An exothermic decomposition detector is configured to detect, through an infrared sensor, the decomposition of the gathered particles.

Implementations may include one or more of the following features. For instance, the collection holes may be tapered, and may have sharp edges configured to scrape a surface that contacts them.

The handle-bar may be configured to move in a radial motion. The handle-bar may include a conductivity sensor configured to detect the presence of skin. The conductivity sensor may be configured to determine if two hands are being used to grip the handle-bar.

Also, the gate may be shaped with a curve that is designed to conform to the shape of part of a human body. The gate may swing out only when the handle-bar is moved. The movement of the gate, or the concurrent movement of the gate and of the handle-bar, may present a path for the user to traverse. Either the gate or the handle-bar, or both, may employ less resistance to movement for slow movements than for quick movements.

The analyzing system may be configured to detect particles other than explosive particles.

The system may also include a blower to create the vacuum in the collection holes and the in-drawing vent, and the air pressure for the outward vent. One blower may be used for the collection holes in the handle-bar and the gate, and the in-drawing vent, and a second blower may be used for the outward vent.

In another general aspect, a trace sample detection system includes a gathering device configured to gather particles through at least two or more of a handle-bar, a gate, and an air-stream gatherer. The handle-bar includes collection holes positioned to be adjacent to a user's hand when the user grips the handle-bar, and the gate includes a series of collection holes positioned to be adjacent to the user's clothing when the user traverses the gate. The air-stream gatherer includes an outward vent and an in-drawing vent positioned to enable objects to be placed between the outward and in-drawing vents. An analyzing device is configured to analyze gathered particles from the gathering device for properties that are indicative of the presence of particles of explosive materials.

Implementations may include one or more of the features noted above.

In another general aspect, trace sampling detection includes gathering particles through two or more of a handle-bar, a gate and an air-stream gatherer, and analyzing the gathered particles for properties that are indicative of the presence of particles of explosive materials.

In another general aspect, a trace sampling detection system includes a gathering device configured to gather particles through one or more collection holes and an impact collector configured to deposit gathered particles onto a portion of a sample media. The system also includes a carousel wheel including the sample media. The carousel wheel is configured to rotate the sample wheel such that the portion of the sample media including the deposited gathered particles is presented to an exothermic decomposition detector. The system further includes an exothermic decomposition detector configured to detect, through an infrared sensor, decomposition of heated materials.

Implementations may include one or more of the following features. For instance the carousel wheel may be configured to heat the sample media resistively. The sample media may be configured to be resistively heated by running a current through the sample media. The sample media may be configured such that the same portion of the sample media may be reused through multiple exposures to the impact collector and the exothermic decomposition detector. The exothermic decomposition detector may be configured to heat the sample media radiatively. The carousel wheel may be replaced with a reel-to-reel mechanism.

In a further general aspect, a transportation mechanism for a particle detection system that includes a gathering device, an impact collector configured to deposit gathered particles, and an exothermic decomposition detector configured to detect decomposition of a deposited material includes a carousel wheel including a sample media configured to accept a deposit of material from the impact collector. The carousel wheel is configured to rotate the sample wheel such that the portion of the sample media including the deposited gathered particles is presented to the exothermic decomposition detector.

The details of one or more implementations are set forth in the accompanying drawings and the description below. Other features and advantages will be apparent from the description and drawings, and from the claims.

DESCRIPTION OF DRAWINGS

FIG. 6 illustrates a method of detecting particles.

Like reference symbols in the various drawings indicate like elements.

DETAILED DESCRIPTION

People who handle or work with explosives, drugs, or other materials typically become contaminated with trace residue of the materials. For example, explosive particles may remain on the hands following manufacturing and/or handling of a bomb or explosive material, and some of these particles are may be transferred to the person's clothing, such as the front pockets and the fly area of the person's pants. Such trace residue may also be transferred onto items such as wallets, spectacles, keys, purses, and door handles, and serves to re-contaminate the hands, even when they are washed and the person changes clothing.

In order to thwart sample collection methods such as pressing a button or ticket, or atmospheric testing, a contaminated person, may take precautions, such as washing of the hands immediately prior to entering a security checkpoint. Sampling material from multiple locations on an individual's body while applying a shearing force to release particles increases the difficulty of thwarting such detection attempts.

Sampling techniques described in this document will work in a variety of situations and locations. For example, the sampling techniques may be employed with train and aircraft passengers, as well as at other location where it is necessary to prevent the transport of explosives or other materials, or to determine if someone has handled explosives or other materials. The trace sampling technologies are not limited by many temperature extremes, and can be installed in a broad range of operational environments, indoor or outdoor.

Although the following discussion is directed to explosive detection, other particles may be detected. Specifically, the system and methods discussed below may be used to gather, collect, and detect hazardous chemicals, illicit drugs, chemical and/or biological warfare agents, or other materials that may leave trace particles. Further, although the following discussion is directed towards people, many of the techniques described below could be used to detect other objects with minimal adjustment. For example, luggage on a conveyer belt could be sent through a similar turnstile system with minor modifications to the samplers.

Figure 1A:
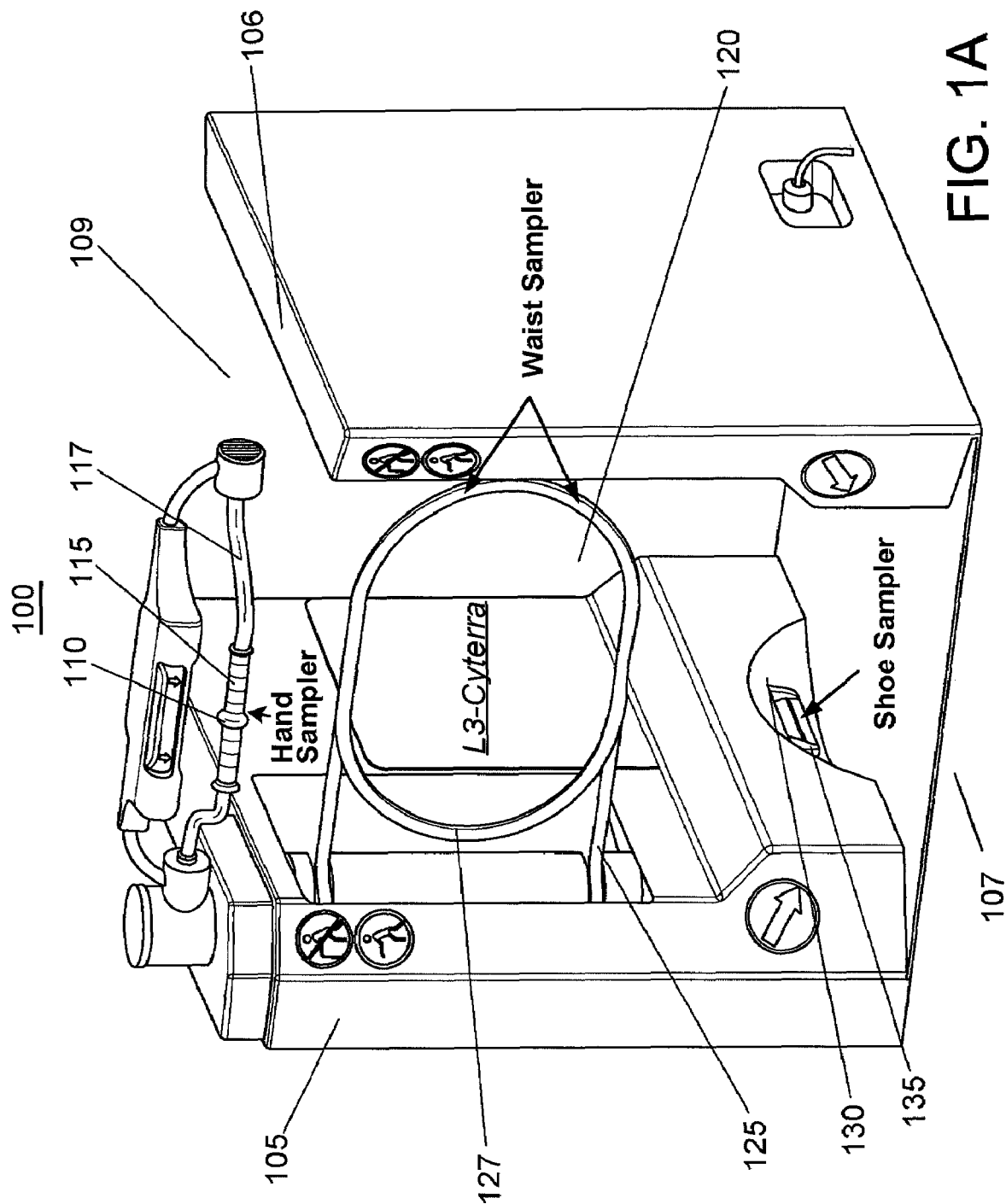
FIGS. 1A, 1B, and 1C illustrate views of an exemplary collection device for collecting samples of material.
Figure 1B:
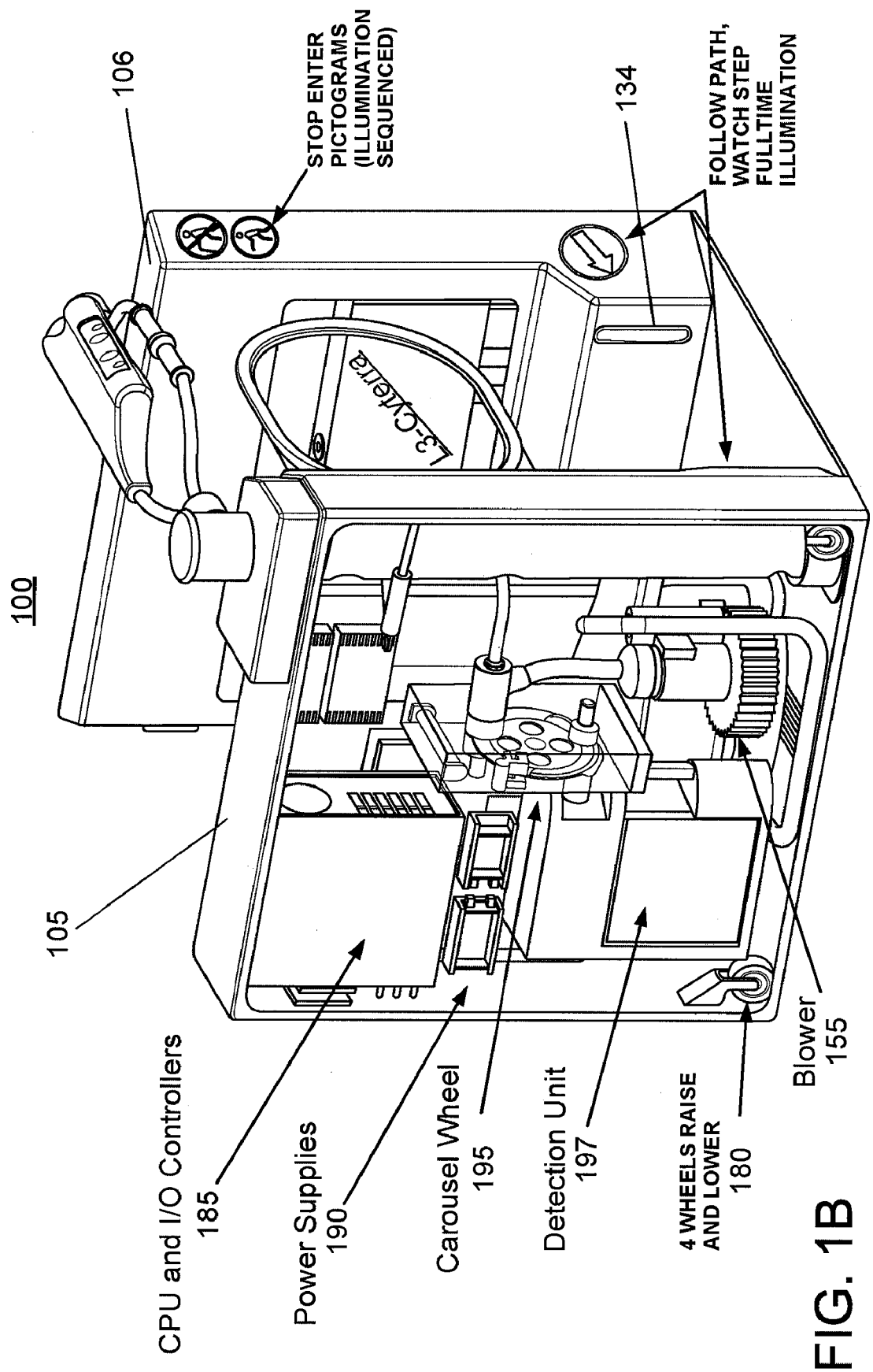
Figure 1C:
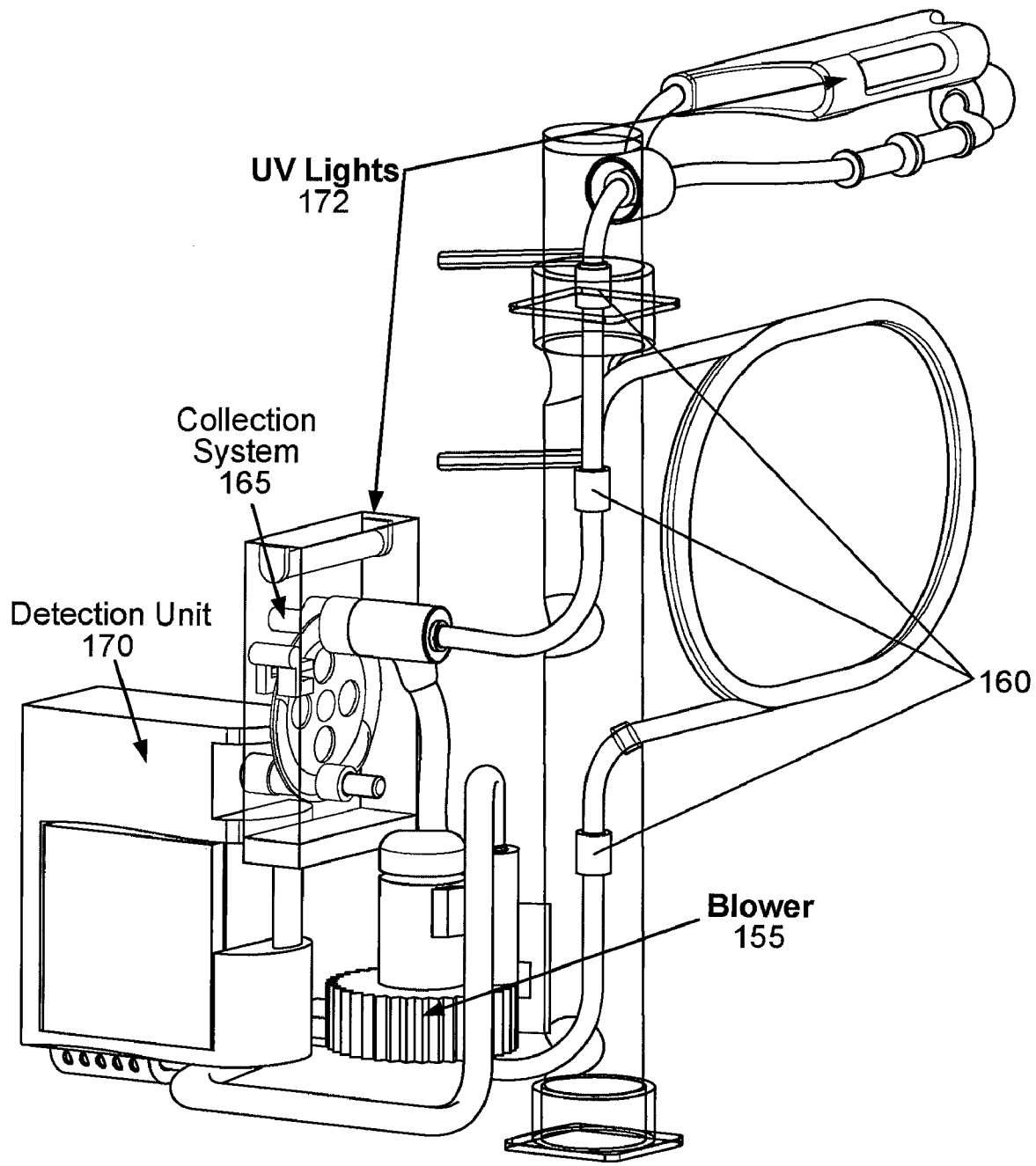

Referring to FIGS. 1A-1C, a collection device 100 includes material collection mechanisms in an explosive trace sampling and detection turnstile system. The collection device 100 includes pedestals 105 and 106, an entrance 107, an exit 109, a hand sampler 110, a torso or waist sampler 120, and a shoe sampler 130 with sampling techniques directed to each corresponding area of the body.

In the device 100, passengers traverse a passage which is defined by the pedestals 105 and 106. The passage includes an entrance 107, a walkthrough space including the samplers 110-130, and an exit 109. In various implementations, the entrance 107 or exit 109 is presented by the motion of the hand and torso samplers 110 and 120. Each of the samplers 110-130 includes collection holes which draw in materials such as explosive particles for analysis. Each of the samplers 110-130 may also include an associated movement or action designed to increase the number of particles that will be gathered. With sufficient pressure and shear force, explosive particles will be extracted from the hand, torso, or shoe areas. In particular, the hand and torso samplers 110 and 120 dislodge and collect samples of material through contact, and the shoe sampler employs a directional air stream to dislodge particles from pants, cuffs, and shoes, and push the particles to the shoe sampler 130.

The collection device 100 may be integrated into a small-profile walkthrough turnstile, as shown in FIGS. 1A-1C. As a passenger passes through the turnstile, the collection device 100 automatically screens a passenger's hands, torso, and feet for trace explosives.

In the implementation shown, the passenger pushes the hand sampler 110 down to unlock the turnstile gate that includes the torso sampler 120. When the passenger grasps the hand sampler 110 at grips 115, suction in the interior of tube 117 dislodges particles on the passenger's hands and draws the particles in through the collection holes on the grips 115 of the hand sampler 110. In one implementation, the hand-sampler 110 may move in two motions. Specifically, in the first motion, the handle-bar may traverse 30-90° of a circumference of a circle vertically downward from the position shown in order to rotate the surface area of the grips 115 with respect to the surface area of the hand(s) pushing down. In the second motion, the handle-sampler 110 may traverse 60-90° of a circumference of a circle horizontally from the position shown. The first and second motions may occur concurrently or separately.

As the passenger moves through the turnstile, the torso sampler 120 brushes against the waist/torso area of the passenger, and suction in the interior of tube 125 dislodges particles from the passenger's waist and draws the particles in through the collection holes 127 of the waist sampler 125. In one implementation, the torso sampler 120 traverses 60-90° of a circumference of a circle horizontally outward from the position shown, similar to the hand sampler 110. The combination of the movement of the hand and torso samplers 120 present the entrance 107 which enables the passenger to traverse the collection device 100.

While the passenger moves and/or traverses the hand and torso samplers 110 and 120, the shoe sampler 130 directs a stream of air from an outlet port 134 (shown in FIG. 1B) to an inlet port 135. Specifically, the stream of air moves towards the passenger's shoe/pant cuff area to dislodge particles and, with the dislodge particles, is drawn into the shoe sampler 130 through the inlet port 135. The hand sampler 110 and torso sampler 120 may both be locked closed and only unlock when certain conditions are met. In one implementation, the outlet port 134 is on the right pedestal 106, while the inlet port 135 is on the left pedestal 105. The air streams from the samples 110-130 are joined inside the pedestal 105 through "Y" type connections so as to enable the three samplers 110-130 to impact on the sample media simultaneously as described with respect to FIG. 3.

The collection device 100 may include a pressure switch on the floor just before the entrance to the turnstile, or a proximity sensor at the entrance to detect the presence of the passenger. A detected presence may control system components, such as, for example, the status of a blower, or the locking or unlocking of the hand and torso samplers 110 and 120.

Components of the system may be constructed using a variety of materials, such as, but not limited to, aluminum, steel, glass, plastic or composite. Metals such as aluminum or steel may interfere with the operation of standard walk-through metal detectors if they are in close proximity to the collection device 100. Composite or plastic materials may be used to avoid such interference.

In one implementation, the target sample rate is about 360 passengers per hour through the system, corresponding to 6 passengers per minute. This rate is determined by three main factors. One factor is the time taken takes by the passenger to pass through the turnstile.

The second factor is the analysis time, which includes the time required to transport the sample to the analyzer, the time required for analysis of the material, and the time required to calculate results using the data produced by the analyzer. In some implementations, the analysis functions may be operated in a pipelined manner such that, for example, a first sample is analyzed while a second sample is being collected and transported to the analyzer.

The final controlling factor is one of choreography. For example, if the turnstile is capable of accepting a passenger every five seconds, to maximize efficiency, the passengers need to present themselves to the turnstile in that amount of time.

Referring particularly to FIGS. 1B and 1C, internal components of the collection device 100 include a blower 155 operating in a vacuum mode, a multi-area trace particle sampling and transport mechanism 160, a collection system 165, a detection unit or detector 170, retractable wheels 180, a computer system 185, a power supply 190, a carousel wheel 195, and a detection unit 197. Other implementations of the collection device 100 may include other components, such as, for example, a boarding pass reader, a wireless link unit, or a system controller including a TCP/IP interface to an airport security network.

The blower 155 provides the necessary vacuum to operate the samplers 110-130 and may be on continuously during operation of the collection device 100, or may include a "standby" mode in which the blower is turned on when activated by the operator, or when a passenger sensor senses a passenger approaching or entering the turnstile. The specific type of blower 155 may be selected depending on desired parameters such as required output, power consumption, or noise level. The blower 155 may be a high quality regenerative blower, such as, for example, the Gast Regenair Model R3105-12. In one implementation, a second blower is used to generate the air flow for the shoe sampler 130.

The multi-area trace particle sampling and transport mechanism 160 is enabled by efficiently transporting trace explosives particles down tubing to a collection system 165 without significant loss to the interior walls of the piping. Small particles of explosives are known to be unusually "sticky," as the explosive crystals are often coated in oils, waxes or polymers. One way to prevent the particles from sticking (or at least to reduce the number of particles that stick) is to minimize the number of particles that reach the interior surfaces. This may be accomplished through design parameters such as, for example, maintaining proper velocity (e.g., greater than 10 m/s) within the transport piping, using gentle bend radii (e.g., greater than 8 times the diameter of the pipe), and having inlet holes that are sized to create a vacuum effect. Additionally, inside surfaces should be smooth and free of abrupt transitions. In one implementation employing the above parameters, particles ranging in size from 5 to 300 microns may be entrained in a flow with a Reynolds Number between 10,000 and 50,000, with near 100% transport efficiency.

The collection system 165 is used to gather transported material particles so that the material may be analyzed by the detector 170. Various collector systems 165, such as a carousel wheel or reel-to-reel ribbon system, which has multiple sample media collection stations or portions, may be used. In the collection system 165, the material is gathered on a sample media that is presented to the detector 170 for analysis. During gathering, the collection system 165 may be sealed against the collection material.

One implementation employs contamination controlling software that controls positioning of the sample media such that, if a given station or portion of the sample media is deemed contaminated, that station or portion is skipped until cleaning or replacement of the sample media. Depending on implementation, the sample media needs to be replaced or cleaned at different intervals (e.g., daily or monthly).

As noted above, the collection device 100 also includes retractable wheels 180, a computer system 185, and a power supply 190. The retractable wheels 180 are used to simplify transportation of the turnstile 175. The wheels may be raised (i.e., retracted into the walls of the device) by use of one of several mechanisms, such as a jackscrew, a cam-lever, or a hex-bolt.

The computer system 185 may include a single CPU or multiple computers. In an implementation including two CPUs, one CPU is directed to controlling the turnstile system 100, and the second CPU is directed to analyzing data. Included in the computer system 185 are application specific boards such as an I/O (input/output) digital controller with an integral A/D (analog/digital) and D/A (digital/analog) converter such as devices manufactured by National Instruments. A monitor and keyboard may be included to accept user input or for service and maintenance. In one implementation, a small LCD VGA monitor with either a touchscreen or a keyboard is permanently connected to the computer system 185 and placed behind an access panel.

To enable compatibility with various supplied voltages, the line voltage may be converted by the power supply 190 to feed DC components. In one implementation, the power supply 190 operates to convert 110/220 VAC, 50/60 Hz to the required output(s). A small UPS (uninterrupted power supply) may be included to enable completion of any sampling or analysis in progress if a power failure occurs, as well as to enable a clean shut down of the computer system 185 in the event of a power failure.

The collection device 100 may further include a carousel wheel 195 and detection unit 197. The carousel wheel 195 includes a sample media configured to hold the sample material as described with respect to FIG. 4A. The detection unit 197 analyzes the sample material on the sample media as described with respect to FIG. 4B.

Figure 2:
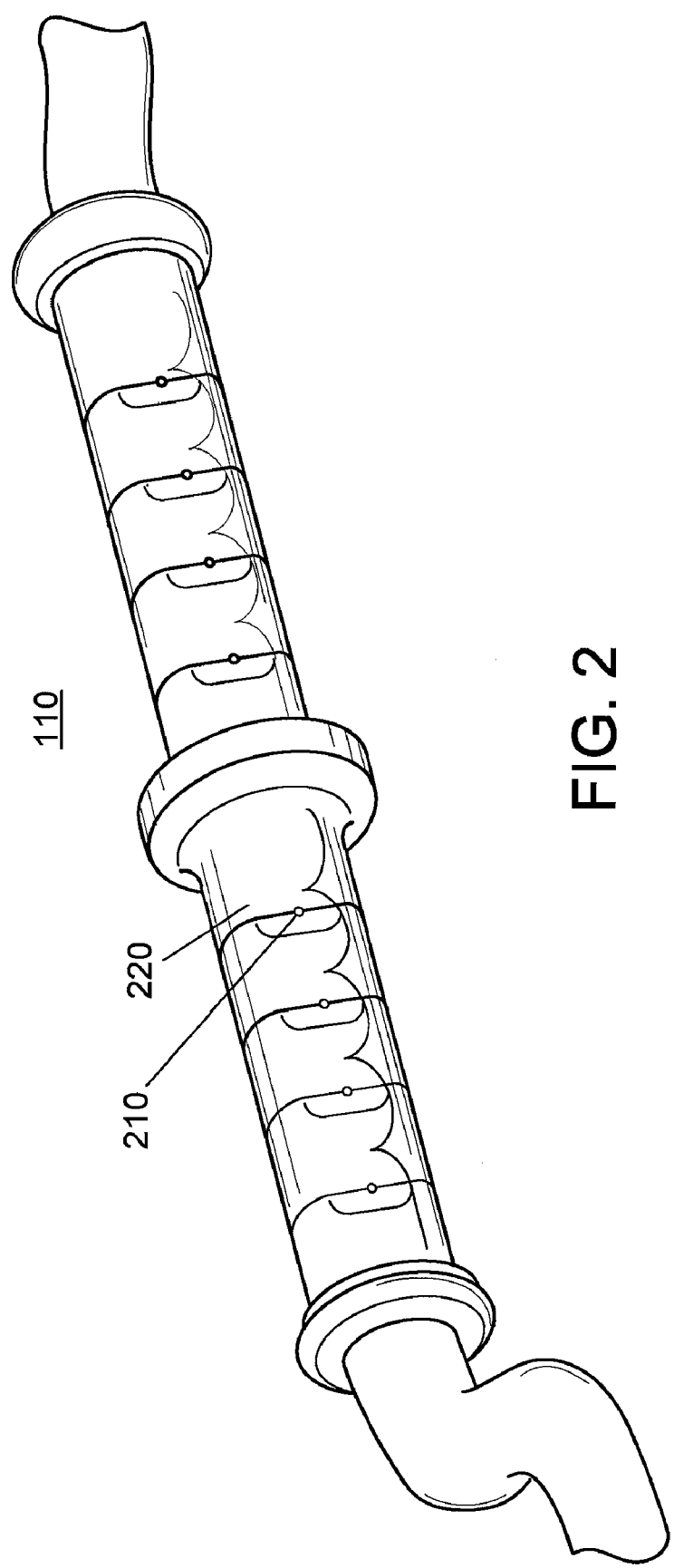
FIG. 2 illustrates an exemplary hand sampler.

Referring to FIG. 2, an exemplary hand sampler 110 includes collection holes 210 and hole contours 220. The hand sampler 110 may be used in the device 100 of FIGS. 1A-1C. In the hand sampler 110, trace sampling of hand(s) occurs as the passenger moves the handle-bar on the hand sampler 110.

The hand sampler 110 has a right and left hand section which may each include collection holes 210 to vacuum the hand during the sampling process. In certain implementations, each of the two sections also may have a conductivity meter to determine that the passenger is using both hands to hold the hand sampler, and that the passenger is not wearing gloves. Since it is desired to have some wiping motion to create sheer and pressure forces between the handle-bar and the hand of the passenger, the design is such that the passenger needs to push the handle-bar down, in a motion similar to that typically used, for example, to unlock the brakes of luggage carts at airports. The handle-bar may move downward along an arcuate path, such that the handle-bar rotates with respect to a downward pressing hand. Both the mechanical motion of pushing the handle-bar down and a conductivity meter reading indicative of skin may be required to unlock the hand sampler 110 and torso sampler 120 allowing them to rotate and thus allowing the passenger to pass through the collection device 100.

Air and particles suspended in the air are drawn in for collection and detection through the collection holes 210. As explosive particles may be wedged in rough surfaces (e.g., skin or clothing), the hand sampler 110 is designed to place a pressure and shear force on a passenger's hands concurrent with the intake of dislodged sample material. The hole contours 220 are shaped to ensure an appropriate pressure and sheer force is generated locally around the collection holes 210. In one implementation, the hole contours 220 are flared or "V" shaped such that the effective collection area is larger than the diameters of the collection holes. The edges of the hole contours 220 or collection holes 210 may be sharp, abrupt, or otherwise shaped to facilitate a scraping movement. As with all three samplers 110-130, the number of collection holes 210 on the hand sampler 110 is a design feature and may vary depending on desired characteristics. In particular, more or larger collection holes 210 increases the amount of gathered material for analysis while also increasing the size and power requirements of the blower(s).

As particles are dislodged, they are vacuumed into the system. A hand-release mechanism on the gate is designed to ensure contact with the finger tips, and the downward pressure applied to the hand bar optimizes the sampling conditions. Optionally, a protective panel above the hand bar houses a UV sterilizer 172 as shown in FIG. 1C, and also serves to ensure that the bar may only be pushed with the hand, and not with the elbow or a handheld item.

One particular implementation includes a 6 mm innerdiameter hole at the end of the hand sampler 110 to develop at least a 10 m/s linear gas velocity inside the hand sampler 110. The sampling section has collection holes 210 which may be angled at 45° to the direction of flow for each hand. Depending on implementation, the grip may be operated with one or both hands. Each collection hole 210 is at the apex of approximately 1 cm wide and 1 cm long V-shaped hole contour 220. Each hole has about 1.5 mm inner-diameter, with the velocity at the hole being 105 to 110 m/s, and the linear velocity in the pipe being 10 to 15 m/sec. The flow in the pipe is turbulent with a Reynolds number of from 15,000 to 22,000.

Trace sampling of the waist/pocket area occurs as passenger pushes the torso sampler 120 open with the body. The torso sampler 120 may be locked until movement or a conductivity reading of the hand sampler 110 triggers unlocking. As shown, the torso sampler 120 includes an oval shaped gathering tube and a planar surface. Other implementations of the torso sampler 120 may employ different shapes. For example, the gathering tube may be a "U" shaped, and the surface may be curved or otherwise formed to conform to the shape of a body. The torso sampler may include a series of collection holes that are the same or similar to the collection holes 210 on the hand sampler 110. The torso sampler 120 uses close-coupled vacuuming of the clothing surface while applying a shear force. This is achieved by having the passenger push against a swinging tubular door, with the vertical tube section of the door being designed to come into close contact with the body so as to sample the region between mid torso and thighs.

As with the hand sampler 110, particles that are in the path of the collection holes 210 will be mechanically dislodged by the shear force and applied pressure of the lip edges, and then sucked into the collection holes. As the passenger moves past the gate, the vertical part of the tube scrubs the torso from the center of the body to the side, covering about 25% of the total torso surface area.

In one particular implementation, the vertical section of the torso sampler 110 is 50 cm tall, with 18 collection holes. Each collection hole 210 is 1.5 mm in diameter and located at intervals of 1 cm, with a 0.2 cm rounded lip on each V. Each orifice is at the apex of a 1 cm wide and 1 cm long V-shaped indent. The flow velocity at each orifice is between 59 and 110 m/sec. This is sufficient to entrain particles in the 5 to 200 micron size range, without entraining larger particles and hairs. The linear velocity inside the pipe is 10 to 28 m/s. As with the hand sampler, the flow inside the 1 inch diameter pipe is turbulent with a Reynolds number in the 14,000 to 41,000 range.

Both the hand and torso samplers 110 and 120 may be spring loaded to place a resistance of about a few pounds against the passenger. If a passenger moves past the samplers 110-130 too quickly, an insufficient sample may be collected. Optionally, speed of a passenger may be slowed by designing a resistance system that increases exponentially with speed. In particular, a hydraulic or pneumatic resistance system may be included to provide low resistance with slow movement and high resistance with quick movement. Further, the torso sampler 120 may include a significantly higher resistance than the hand sampler 110 at any speed to encourage use of the passenger's torso, rather than the passenger's hands, to push the gate.

In the shoe sampler 130, trace sampling of the shoes and pant cuffs occurs while the passenger stands at the turnstile entrance and begins to pass through the gate. The sampling is conducted by gathering particles from an air stream that is blown out of one or more holes (e.g., the outlet port 134) on one side of the turnstile passage and sucked in through one or more other holes (e.g., the inlet port 135) on the other side of the turnstile passage. In one implementation, an air-knife less than 1 cm in width and 15 cm in height, with a flow rate of 4 liters per sec (l/s) is used to dislodge particles from shoes, boots and pant cuffs, as the passenger walks through the turnstile. The air-knife has benefits over a "puff" based blowing system, in that the gathering ability is continuous and less susceptible to missing areas of passengers. The particles are drawn into the air and then sucked into a vacuum-line at a flow of 6.5 l/s by means of 4 sampling ports of 6 mm innerdiameter. Tapered lower sidewalls of the turnstile minimize the distance between the air-knife and the shoes/pant cuffs, and the distance to the sampling inlet. The air jet and intake ports are positioned to maximize particle collection efficiency.

Once the passenger has completely passed the collection device 100, the hand sampler 110 and torso sampler 120 return to the original start position. Spring loading that is dampened to insure that these two components do not slam shut may be included. After completion of the sampling, the collection device 100 analyzes the sample and may present the results to the operator as either "Clear" or "Alarm."

The previous descriptions provide exemplary implementation of a detection system 100 including a hand sampler 110, a waist/torso sample 120, and a shoe sampler 130. Other implementations may include different features, such as a pressure sensor to detect performance-limiting hole blockage and to automatically prompt a cleaning cycle upon detection of such blockage. Also, sensors (e.g., optical sensors) may be employed to detect passengers climbing, crawling, or otherwise avoiding the samplers. Further, a camera may be included that may take pictures of all passengers or only passengers that test positive for certain materials.

Figure 3:
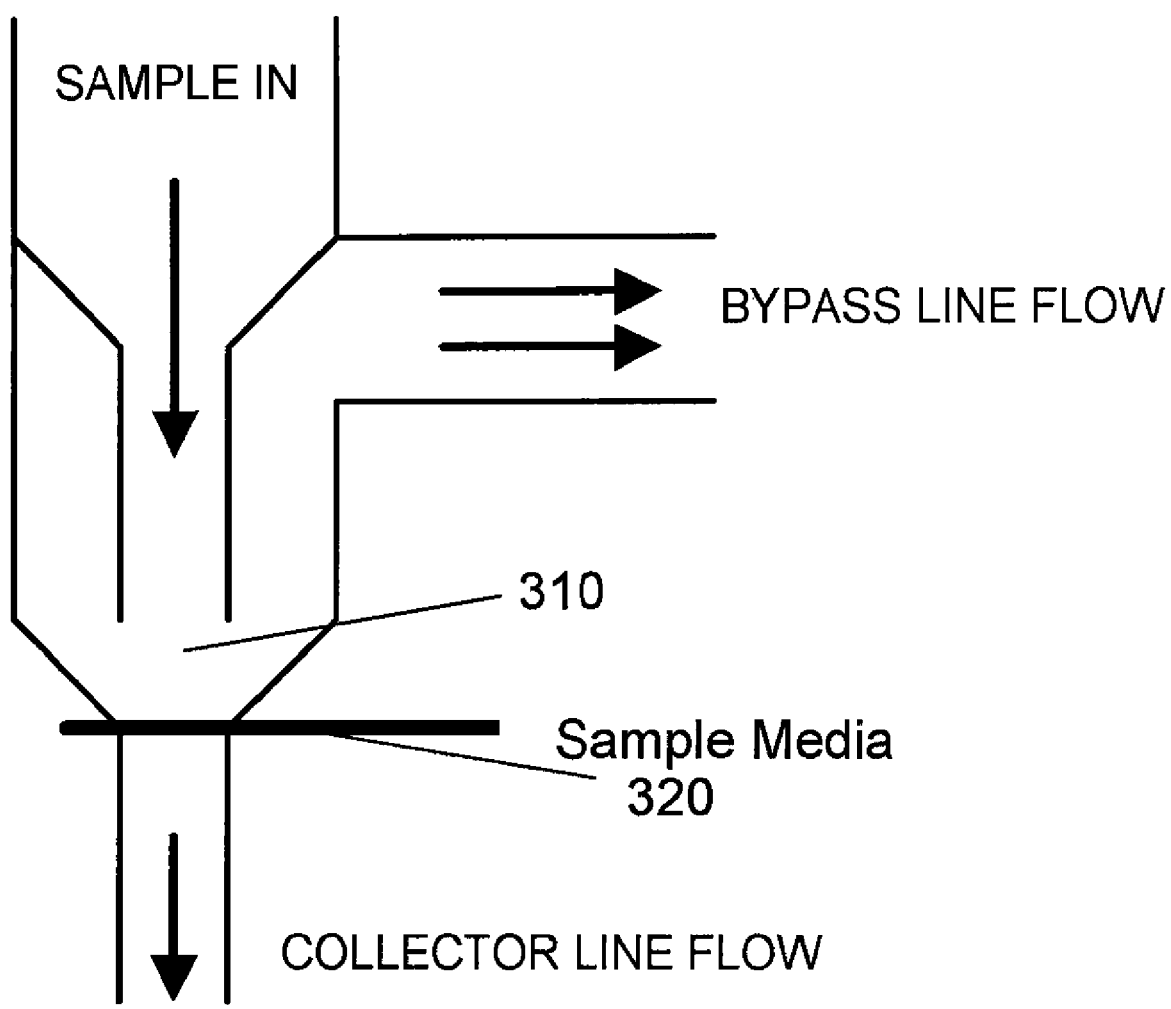
FIG. 3 illustrates an exemplary impact collector.

Referring to FIG. 3, an impact collector 300 combines the air streams of the three samplers into a single air-stream from which particles are collected onto a sample media 320. There is a critical flow to avoid particles falling out of the airflow and onto the tubing walls. One implication of particles falling out of the sample stream is a loss of sample that leads to a false negative. Another implication is one of carry over. Specifically, if a particle falls out of the sample stream, it has the potential of showing up in later samples leading to a false positive. Because of such implications, after every positive sampling, there may be a clearing purge cycle, where the system is run without additional sample material.

In the impact collector 300, the end of the sample tube may be close coupled to the sample media 320. The sample media may be constructed out of a variety of materials, such as, for example, Teflon, stainless steel mesh, carbon fiber, or a deactivated glass wool pad. If resistive heating is being employed, the sample media 320 may need to be conductive. If radiative heating is being employed, conductivity of the sample media 320 is not required.

In the impact collector 300, the air and explosive vapors divide according to the ratio of the bypass flow to the collector flow. Typical collector flows are between 0 and 10 percent of the total flow. Particles, however, are not able to make the 180° turn 310 and thus impact upon the sample media 320. In order to keep the piping of the turnstile clean, valves may be placed downstream of the collection system and kept closed except during the sampling time.

In one particular implementation, the internal inner-diameter of the impact collector 300 is about 1.5 cm. The outer ring is about 3 cm in diameter. If the sample media 320 rotates, the impact collector 300 itself needs to clear the sample media 320. The impact collector 300 may need to seal against the portion of the sample media 320 at the outer ring with the inner tube being from about 0.2-2.0 cm away from the sample media 320. An O-ring may be included on the outer tube to form a seal. In come cases, slight leakage may be acceptable. Depending on implementation, either the impact collector 300 is lowered to form the seal, or the sample media 320 itself is raised to form the seal.

Figure 4A:
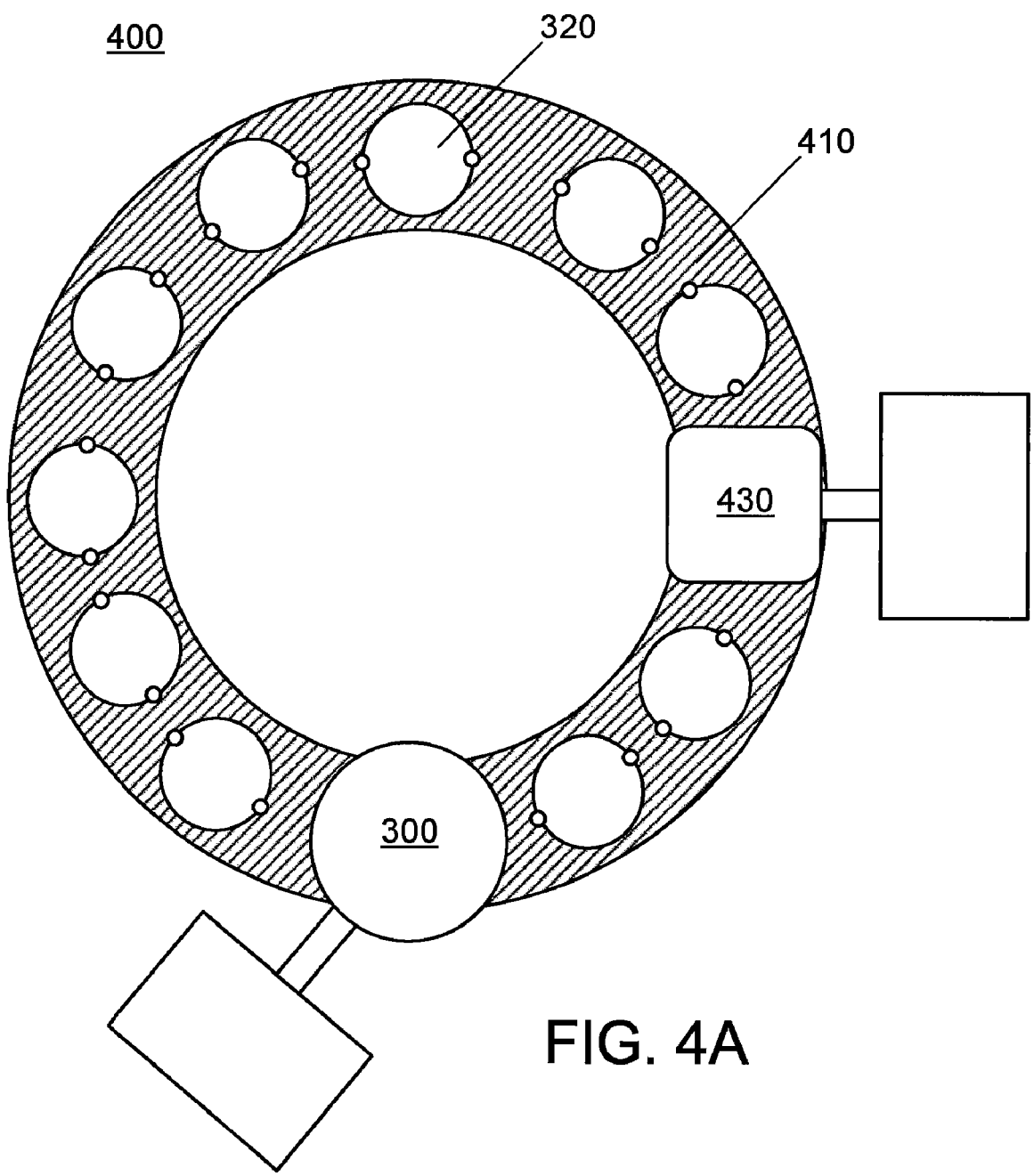
FIGS. 4A and 4B illustrate a top and side view of an exemplary collector and detection system.

Referring to FIG. 4A, a top view of a collection system 400 includes the impact collector 300 and sample media 320 of FIG. 3, and a detection unit 430. In the collection system 400, the impact collector 300 is used to deposit the gathered material onto the sample media 320. The media moving mechanism moves the sample media 320 such that the sample media including the deposited material moves from a region adjacent to the impact collector to a region within the detection unit 430. The deposited material is than analyzed for traces of specific material.

Figure 4B:
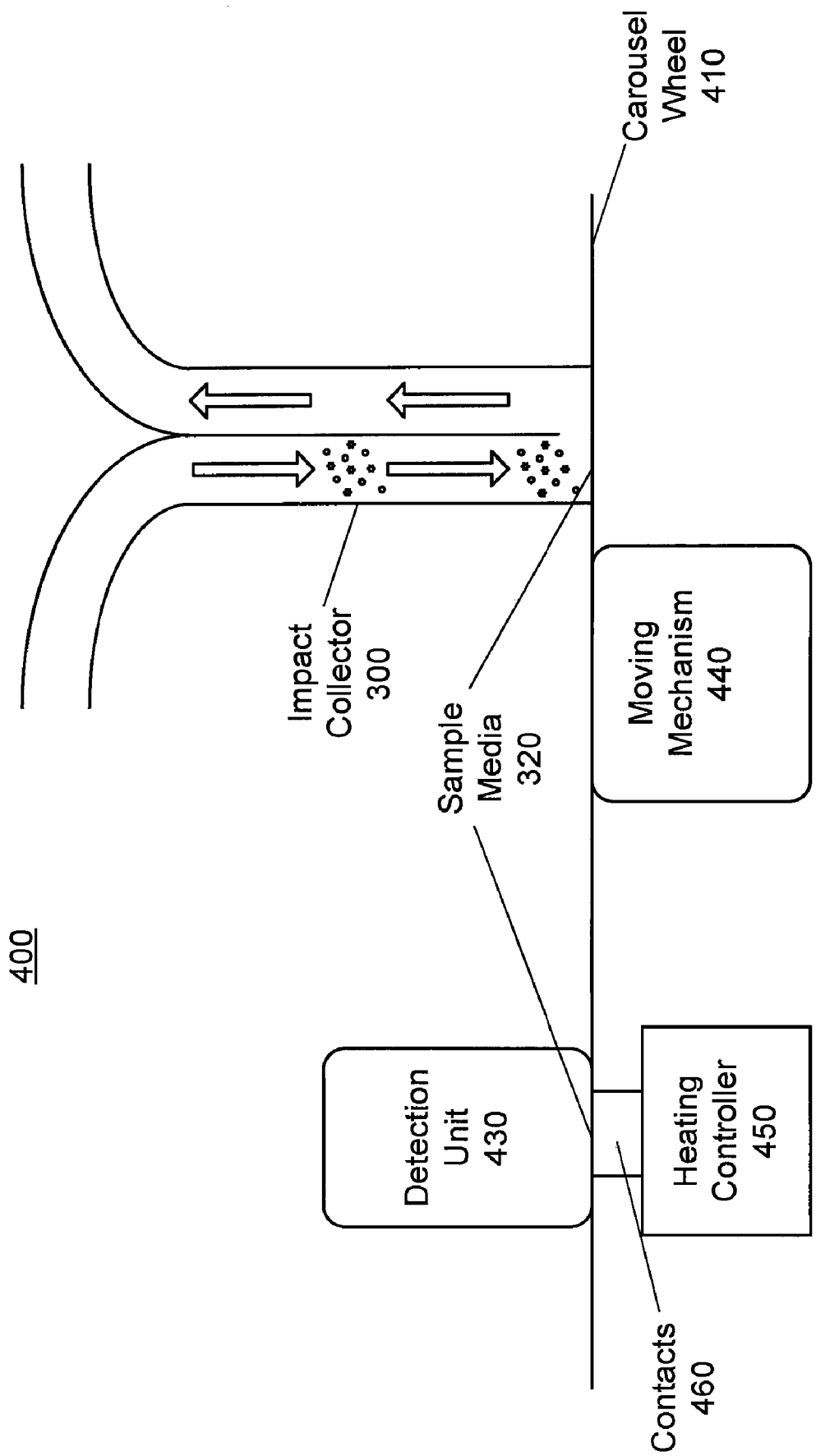

Referring to FIG. 4B, a side view of a collection system 400 includes a media moving mechanism 440, a heating controller 450, and contacts 460. The discussion below refers to two specific implementations directed to resistive and radiative heating exothermic decomposition (with resistive heating shown in FIG. 4B), but other methods of initiating thermal decomposition may also be used. In particular, elevating the temperature of a particle by using electromagnetic radiation, lasers, the convection of heat via warm air to the particle, or the conduction of heat to the particle would be sufficient for causing thermal decomposition.

The particular collection system 400 to be used may be based on factors such as a desired period between maintenance sessions, ease of maintenance, or cost. FIG. 4 illustrates an implementation involving a carousel wheel 410 with a reusable discreet sample media 320. Other implementations, such as a "reel-to-reel" system with a one time or reusable sample media 320, also may be used. Such a reel-to-reel mechanism may be more costly to build and more difficult to maintain (e.g., by replacing the worn sample media 320) than the carousel mechanism of 400. Because the reel-to-reel mechanism could hold more sample media, the time between replacements would be greater than for the carousel implementation.

In the illustrated implementation having a carousel wheel 410, the sample media 320 is within the carousel wheel 410 and includes either a series of discreet collecting areas or a continuous collecting area. In a series of steps, the collection system 400 gathers collected material onto an area of the sample media 320 and then rotates to a detection unit 430 to enable the deposited material to be analyzed by a detection unit to detect the presence of particles of materials.

According to various implementations employing the carousel wheel, a first station is the impact collector 300, which may seal to the carousel wheel 410. The term "station" refers to specific locations or degrees of rotation of the carousel wheel 410. The position of stations may be determined by the position of holes along the circumference at angular positions of the carousel wheel 410. After particles are deposited with the impact collector 300 to an area of the sample media 320, the carousel wheel 410 rotates to the second station, which is the detection unit 430. Characteristics of the detection unit 430 depend on the detection unit employed. If the detection unit is a thermal desorber, the detection unit may clamp over the gathered material which is vaporized.

The actual detection unit chosen may vary based on desired characteristics, such as complexity, cost, or sensitivity. Various detection units may be employed, such as an ion mobility detector (IMS), gas chromatography coupled with a chemiluminescence detector (GC-CL), a thermal desorber, a resistive heating exothermic decomposition detector, or a radiative heating exothermic decomposition detector.

A media moving mechanism 440 is employed to rotate the sample media 320, and in the implementation discussed above, the carousel wheel 410. For a high degree of positional accuracy, a stepper motor may be employed. As a stepper motor is expensive and requires specialized electronics to control, a simpler alternative that may be used is a unidirectional or bidirectional DC motor. An LED optical sensor may be used to determine and control the position of the media moving mechanism 440. Maintenance of the carousel wheel 410 may be conducted through an automatic disc loading and unloading station to extend the time between routine replacement of the sample media to, for example, one month.

In one implementation that includes a resistive heating exothermic decomposition detector (discussed below), the sample media 320 area is three $cm^2$ and includes two contacts 460 which are placed at opposite ends of the sample media 320. The contacts 460 may be shaped in various ways, such as, for example, raised metallic bumps (e.g., like a contact for a battery), rods, or plates. A spring loaded contact may be used to complete the connection. The sample media 320 may be designed with upper and lower halves. In one assembly method, the two halves are separated, the sample media 320 is installed on the bottom half, and the top half is attached on top of the sample media 320 forming a sandwich. In one implementation, for each portion of the sample media 320, one of the contacts 460 is in the form of an electrode which is tied to a single common connection point (not shown), and the other contact 460 is a unique connection (as shown in FIG. 4B). In such an implementation, the common connection point is constantly connected to the power supply, and only one unique connection is connected at a time to enable only one portion to be resistively heated. The sample media may include holes for the optical sensors (or LED sensor as discussed above with respect to the carousel wheel 410 implementation).

Residual material, such as oils, may contaminate or mask later measurements, or may shorten the life of a reusable sample media 320. By heating the sample media 320 to a higher temperature than that required to trigger decomposition of energetic material, such residual material may be burned off. Optionally, a high temperature bake out at temperatures in excess of 300° C. may be conducted at the second station or a separate third station in order to thermally decompose remaining particles. A bake out at a third station may be particularly useful in implementations without resistive or radiative heating, such as an IMS or GC-CL system with thermal vaporization.

In one implementation, the real-time temperature of the sample media 320 is measured through a pyrometer, and such measurement is a part of a feedback loop to enable the temperature to be actively controlled. The pyrometer may be included in the detection unit 430 or the heating controller 450. During heating, there is slight expansion of the sample media 320. In order to prevent distortion, the design is such that there is a slight tension on the sample media 320.

Detecting trace amounts of explosives remains a challenging task and often suffers from poor sensitivity to minute amounts of explosives and low throughput. These issues can be addressed by relying on the rapid kinetics and thermodynamics associated with the thermal decomposition of explosives. Although most molecules decompose endothermically when heated in an atmosphere deprived of oxygen, an explosive compound decomposes exothermically releasing heat to the environment. The released heat is immediately transferred to the molecules surrounding the decomposing explosives, which results in a localized increase in temperature that provides a measurable indicator of an explosive compound.

Specifically, explosive compounds decompose exothermically (they release heat to the surroundings) when heated anaerobically. If the mass of the explosives is large enough, the temperature rises, which accelerates the reaction rate even further, releasing additional heat, and culminating in a runaway thermal explosion. For sub-critical masses, the material is consumed before it explodes as heat is lost to the surroundings. Nevertheless, even for these sub-critical cases, the temperature rises above its surroundings before decaying back to the ambient.

A resistive heating exothermic decomposition detector senses the thermal energy released during exothermic decomposition, which is a thermodynamic property unique to energetic materials. This feature makes it possible to detect explosives, including nitro-organics and nitro-salts, peroxides, perchlorates, and gun powder, as well as homemade explosives of as yet unknown composition.

The heat released from small amounts of explosives during decomposition may be detected by using the IR detection array to detect the thermal signature resulting from this process. The camera is configured to detect heat in the mid-wave infrared (MWIR), 3 to 5 micron wavelength, or long-wave infrared (LWIR), 8 to 12 micron wavelength, regions to observe the temperature of the environment surrounding an explosive particle. Thermal imaging cameras employing detection in the MWIR region benefit from superior resolution and contrast while those detecting in the LWIR region offer enhanced sensitivity to smaller temperature fluctuations and are less affected by atmospheric conditions (e.g., LWIR radiation can be transmitted through mist and smoke).

For trace explosive decomposition, the inherently small particle sizes complicate the detection process. For an explosive compound undergoing anaerobic thermal decomposition, the heat released is expected to be equivalent to about a 100° C. temperature rise in a 200° C. environment within a five to five hundred millisecond time frame, depending upon the type of explosive, its mass, the heating rate and the rate of heat loss. In some cases, the time frame is 5 to 30 milliseconds. If all of the exothermic energy produced by the decomposition of the explosive occupied one instantaneous field of view (IFOV) of the IR detection array, this would be easily detectable, since most MWIR/LWIR cameras have sensitivities near 0.05° C. However, trace amounts of explosive particles emitting this heat weigh as little as a few nanograms and their emitted energy would only occupy a region 0.1 to 0.01 millimeters in diameter. Since the IFOV per pixel of a typical camera lens is about two millimeters in diameter at close range (approximately one foot away from the source), the released energy from a trace explosive is undetectable across the IFOV area. In this case, the temperature rise has been diluted across the entire IFOV and appears as a temperature increase as small as 0.003° C. for a nanogram-size particle.

In order to detect localized heat signatures, the IR detection array is appropriately configured to record fast, microscopic reactions. Because of these constraints, the camera has a macro (close-up) lens capable of achieving an IFOV of less than between 50 and 150 microns in diameter per pixel. In addition, the resolution of the camera is sufficient to provide numerous individual pixels which act as their own individual heat detectors and serve to increase the sensitivity of the detection of energetic particles. For example, doubling the resolution of a thermal imaging camera leads to a ×4 to ×8 lowering of the lower detection limit of this method. Using a camera with a sensitivity of 0.05° C., a trace explosive decomposition could be easily detected with a signal to noise somewhere between 100 and 200 (with a signal to noise of 40 as the video threshold for the human eye). A final technical challenge arises due to the speed of the thermal decomposition process. If the camera integration time between frames is long relative to the energy release, the energy is time averaged and may not be captured by the camera. For example, for a five to ten millisecond reaction and using a 60 Hz (16 ms) imaging rate, the observed energy released from an energetic particle is reduced by less than a factor of 3. This yields a signal to noise ratio somewhere between 40 and 80.

In one implementation, the IR detector array is a long wave infra red detector (LWIR) that is sensitive in the 7.5 to 14 micron range. The detector is equipped with a focusing lens in order to resolve pixels down to about 50 microns. The refresh rate of the system is 60 Hz. The detector is a 320×240 array with 76,800 pixels. The sensitivity of each pixel is specified as 0.05° C., which facilitates sensitivity at the mid-picogram level. Since the particle mass is inversely proportional to the third power of the pixel size, the sensitivity can be enhanced by using a more powerful focusing lens.

Analytical interpretation of the results is possible by examining the temperature of individual pixels or the average of several pixels as a function of time. Results may demonstrate that a particle's rapid increase in temperature exceed that of the sample media 320. This feature can be used in algorithms to automatically detect the presence of explosives. In particular, each energetic compound has a quantifiable and positive heat of decomposition (H) and a quantifiable activation energy (E). H impacts the total heat that is released and E the rate of heat release. These two properties interact in such a way that a detector may distinguish classes of explosives and/or the chemical composition.

Automatic algorithm based target recognition is used to track multiple pixels simultaneously and to automatically recognize the unique characteristics of explosives. Simple enhancements include subtraction of the varying background temperature, and displaying the differential so as to better visualize the peak maximum. Local maxima in a temperature versus time plot are indicative of the presence of explosives and are mathematically defined as points at which the time rate of change of the temperature equals zero (i.e., $dT/dt=0$). However, both local maxima due to the fluctuating temperature of the sample media 320 may also be present. To correct for these artifacts, the sample media 320 temperature may be subtracted from the temperature recorded at various points.

Specifically, in one implementation, the analysis of the sample collected on the sample media 320 may be performed by heating the collection area from ambient to about 300° C. in one to two seconds. This heating may be performed in front of the IR detection array (included in the detection unit 430) one implementation of which includes 320×240 pixels focused on the sample area. Each pixel may view about 100 μm square for a total viewing area of about 2.5×1.5 cm. When the sample media 320 is rotated to the second station, which includes the detection unit 430, heating is performed resistively with about 10 amps at 2 volts.

In a radiative heating implementation, a flash lamp is included in the heating controller. The heating controller 450 and the detection unit 430 may optionally be on the same side of the sample media 320. The flash lamp delivers the necessary activation energy for initiating decomposition of residual explosive particles.

The previous description provides exemplary implementations of a collection system 400 and a detection system 450. Other implementations may include different features, such as a checking solution injected onto the sample media 320 on an infrequent but scheduled basis to test the ability of the system to successfully detect particles of a material. This mechanism may include a reservoir, that needs to be replaced monthly, and may include either the LEE miniature variable volume pump model number LPVX0502600B, (see www.theleeco.com) or a small KNF model UNMP830 (see www.knf.com) or similar pump and a LEE solenoid valve similar to LEE model number INKX051440AA.

Figure 5A:
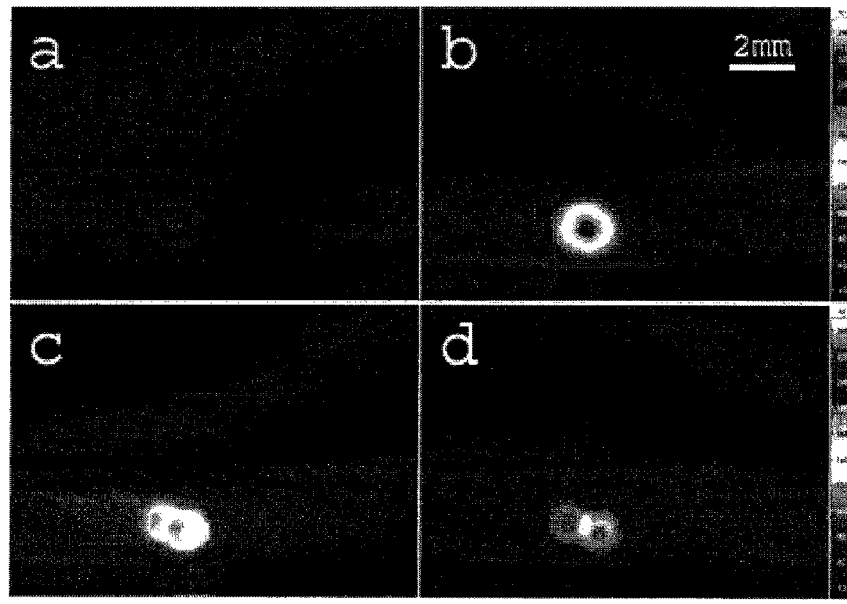
FIGS. 5A and 5B illustrate data results of particle detection.

FIG. 5A shows data results 500 of exothermic decomposition detection. In particular, a picture is shown of a sample media with a decomposing material at four different instances of time. Specifically, data results 500 for the energetic detection of a particle of smokeless powder using a 60 Hz frame rate are shown. Element (a) shows an initial IR image at frame 110 with a relatively cool particle and filament. Next, element (b) shows an IR image at frame 389 showing elevated temperatures around the particle just prior to explosion. Next, element (c) shows an IR image at frame 390 showing the particle explosion. Finally, element (d) shows an IR image at frame 391 showing elevated gas temperatures resulting from the particle explosion.

Figure 5B:
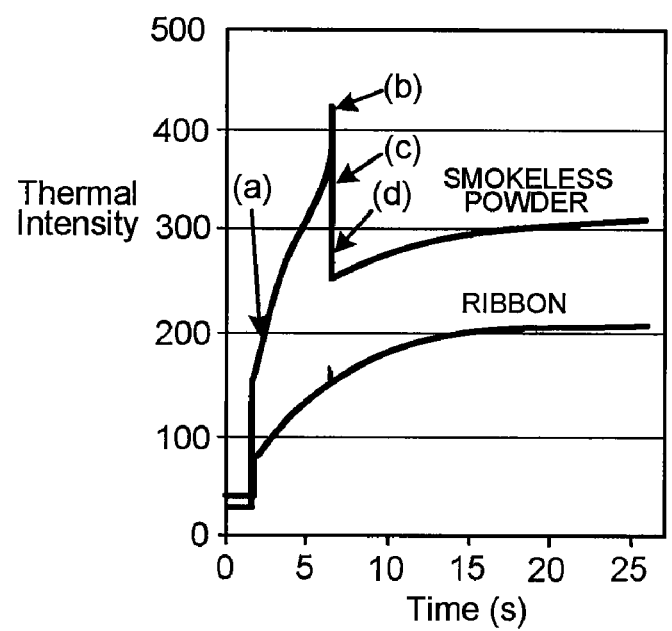

Referring to FIG. 5B, data results 550 for the same decomposition are shown from the perspective of a pixel viewing the smokeless powder and a pixel viewing the sample media across time. In the results, the four instances of time from the results 500 of FIG. 5A are marked. Specifically, a two-dimensional plot of the thermal signature of one pixel near a smokeless pellet and one pixel on the sample media is shown.

Referring to FIG. 6, a method for detecting particles includes gathering the particles from one or more locations, depositing the gathered particles onto a sample media, rotating the sample media to a detection system, and analyzing the gathered particles with the detection system.

Particles are gathered through collection holes (610). As shown in FIG. 1, the collection holes may be distributed across a handle-bar, torso gate, a shoe blower, or other devices. The particles may be gathered through multiple devices concurrently. In one implementation, a passenger pulls down a handle-bar which unlocks a gate that may be pushed with the passenger's torso, all while an air-knife blows particles from the passenger's shoes and cuffs. In particular, friction, pressure, and sheer force are produced by the resistance of the handle-bar, torso gate, and air-stream, which releases dislodged particles for gathering.

The gathered particles are then deposited onto the sample media (620). If gathered from multiple locations, the particles may first be combined into a single stream of particles, and then the single stream may be deposited onto the sample media as shown in FIG. 2. In one implementation, the sample media is reusable and may be moved after a deposition such that a different portion of the sample media is presented for the next deposition.

The gathered particles are presented to a detection unit (630). If the sample media is within a carousel wheel, the carousel wheel is rotated to present the portion of the sample media which includes the gathered particles to the detection unit. In one implementation, after each deposition, the carousel wheel is rotated, and after a number of decompositions, a portion of the sample media is reused.

The gathered particles are analyzed (640) by the detection unit. Either the carousel wheel or the detection unit may heat or radiate the gathered particles to spur decomposition. In one implementation, a current is driven through the sample media to resistively heat the gathered particles while an IR detection array monitors particle decomposition.

The previous description provides exemplary implementations of a method for detecting particles. Other implementations may include different steps, such as, for example, a cleaning cycle may be run after every deposition or analysis. The cleaning cycle may include heating and/or running an air-stream through part or all of the sample media.

What is claimed is:

1. A trace sampling detection system comprising:
a gathering device configured to gather particles through each of:
   a handle-bar including collection holes positioned to be adjacent to a user's hand when the user grips the handle bar, wherein the handle-bar is configured to release particles in response to a grip and motion of the user,
   a gate including a series of collection holes positioned to be adjacent to the user's clothing when the user traverses the gate, wherein the gate is configured to release particles in response to pressure applied from the user and is configured to open only when the handle-bar is moved,
   an air-stream gatherer including an outward vent and an in-drawing vent positioned to enable objects to be placed between the outward and in-drawing vents, wherein the air-stream is configured to release particles from objects that block the air-stream between the outward and in-drawing vent;

a collection tube configured to deposit gathered particles from the gathering device onto a portion of a sample media;

a carousel wheel that includes the sample media and is configured to rotate the sample wheel such that the portion of the sample media including the gathered particles is presented to an exothermic decomposition detector; and an exothermic decomposition detector configured to detect, through an infrared sensor, the decomposition of the gathered particles.

2. The system of claim 1 wherein the collection holes are tapered.

3. The system of claim 1 wherein the collection holes have edges configured to scrape a surface that contacts the edges.

4. The system of claim 1 wherein the handle-bar is configured to move in a radial motion.

5. The system of claim 1 wherein the handle-bar includes a conductivity sensor configured to detect the presence of skin.

6. The system of claim 1 wherein the gate is shaped with a curve that is designed to conform to the shape of part of a human body.

7. The system of claim 1 wherein the movement of the gate presents a path for the user to traverse.

8. The system of claim 1 wherein the gathering device is configured to gather particles concurrently from the handle-bar, gate, and the air-stream gatherer.

9. The system of claim 1 wherein the analyzing system is configured to detect particles other than explosive particles.

10. The system of claim 1 further comprising a blower to create the vacuum in the collection holes and the in-drawing vent.

11. A trace sampling detection system comprising:
   a gathering device configured to gather particles with each of:
      a handle-bar including collection holes positioned to be adjacent to a user's hand when the user grips the handle bar, and
      a gate including a series of collection holes positioned to be adjacent to the user's clothing when the user traverses the gate, wherein the gate is configured to open only when the handle-bar is moved; and
   an analyzing device configured to analyze gathered particles from the gathering device for properties that are indicative of the presence of particles of explosive materials.

12. The system of claim 11 wherein the collection holes are tapered.

13. The system of claim 11 wherein the collection holes have edges configured to scrape a surface that contacts the edges.

14. The system of claim 11 wherein the handle-bar is configured to move in a radial motion.

15. The system of claim 11 wherein the handle-bar includes a conductivity sensor configured to detect the presence of skin.

16. The system of claim 11 wherein the movement of the gate presents a path for the user to traverse.

17. The system of claim 11 wherein either the gate or the handle-bar employs less resistance to movement for slow movements than for quick movements.

18. The system of claim 11 wherein the gathering device is configured to gather particles concurrently from the handle-bar and the gate.

19. The system of claim 11 wherein the analyzing system is configured to detect particles other than explosive particles.

20. A method of trace sampling detection comprising:
   gathering particles with each of:
      a handle-bar including collection holes positioned to be adjacent to a user's hand when the user grips the handle bar, and
      a gate including a series of collection holes positioned to be adjacent to the user's clothing when the user traverses the gate, wherein the gate is configured to open only when the handle-bar is moved; and
   analyzing the gathered particles for properties that are indicative of the presence of particles of explosive materials.

* * * * *

UNITED STATES PATENT AND TRADEMARK OFFICE
CERTIFICATE OF CORRECTION

PATENT NO.         : 7,666,356 B2                                    Page 1 of 1
APPLICATION NO.    : 11/425313
DATED              : February 23, 2010
INVENTOR(S)        : Daniel J. O'Donnell et al.

It is certified that error appears in the above-identified patent and that said Letters Patent is hereby corrected as shown below:

Claim 1
In claim 1, at Col. 14, line 53, replace "handle bar" with --handle-bar--.

Claim 12
In claim 12, at Col. 15, line 38, replace "handle bar" with --handle-bar--.

Claim 22
In claim 22, at Col. 16, line 31, replace "handle bar" with --handle-bar--.

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO.       : 7,666,356 B2                                                      Page 1 of 1
APPLICATION NO.  : 11/425313
DATED            : February 23, 2010
INVENTOR(S)      : O'Donnell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 918 days.

Signed and Sealed this

Seventh Day of December, 2010

David J. Kappos
*Director of the United States Patent and Trademark Office*